(12) United States Patent
Alabaster

(10) Patent No.: US 6,553,386 B1
(45) Date of Patent: *Apr. 22, 2003

(54) SYSTEM AND METHOD FOR COMPUTERIZED VISUAL DIET BEHAVIOR ANALYSIS AND TRAINING

(76) Inventor: Oliver Alabaster, 4318 Adrienne Dr., Alexandria, VA (US) 22309

( * ) Notice: Subject to any disclaimer, the term of this patent is extended or adjusted under 35 U.S.C. 154(b) by 0 days.

This patent is subject to a terminal disclaimer.

(21) Appl. No.: 09/461,664

(22) Filed: Dec. 14, 1999

Related U.S. Application Data

(63) Continuation-in-part of application No. 09/211,392, filed on Dec. 14, 1998.

(51) Int. Cl.[7] ............................................. G06F 17/30
(52) U.S. Cl. ..................... 707/104.1; 707/1; 705/27; 706/16; 345/810; 345/342; 434/137; 600/300
(58) Field of Search ............................ 705/15, 27, 1; 434/127, 262; 128/897, 630; 600/300; 706/16; 345/342, 810; 707/1, 104.1

(56) References Cited

U.S. PATENT DOCUMENTS

| | | | | |
|---|---|---|---|---|
| 4,464,122 A | * | 8/1984 | Fuller et al. ................. | 434/262 |
| 5,412,560 A | * | 5/1995 | Dennison ..................... | 128/630 |
| 5,454,721 A | * | 10/1995 | Kuch ........................... | 434/127 |
| 5,542,420 A | | 8/1996 | Goldman et al. ............. | 600/301 |
| 5,682,330 A | | 10/1997 | Seaman et al. ............... | 358/403 |
| 5,819,245 A | * | 10/1998 | Peterson et al. .............. | 706/16 |
| 5,819,735 A | * | 10/1998 | Mansfield et al. ........... | 600/300 |
| 5,832,446 A | * | 11/1998 | Neuhaus ....................... | 705/1 |
| 5,836,312 A | * | 11/1998 | Moore .......................... | 128/897 |
| 5,845,263 A | * | 12/1998 | Camaisa et al. .............. | 705/27 |
| 6,011,550 A | * | 1/2000 | Capps et al. ................. | 345/342 |
| 6,038,546 A | * | 3/2000 | Ferro ........................... | 705/15 |

* cited by examiner

*Primary Examiner*—Charles Rones
(74) *Attorney, Agent, or Firm*—Piperd Rudnick LLP; Steven B. Kelber

(57) ABSTRACT

A computer database includes information enabling display on a screen of a plurality of objects, in successive groups, together with display of graphics associated with each group. The graphics enable a first user selection of one of the objects of each group and a second user selection related to the object selected by interaction with the screen display, using conventional mouse, touchscreen or other techniques. The user selections are stored in a storage medium so as to generate a database of user choice information from which a behavior analysis is performed. The user selections may comprise food choices and evaluation of enthusiasm, and frequency thereof, whereby a dietary behavior profile is produced. Diet training may then be coordinated by display of a meal and providing the user with the ability to estimate nutrient content as well as participate in interactive adjustment of food items and portion sizes.

44 Claims, 16 Drawing Sheets

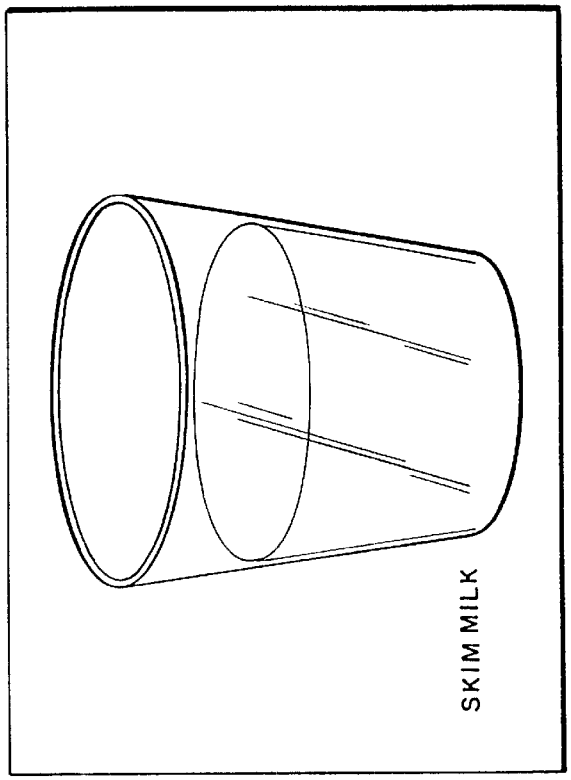
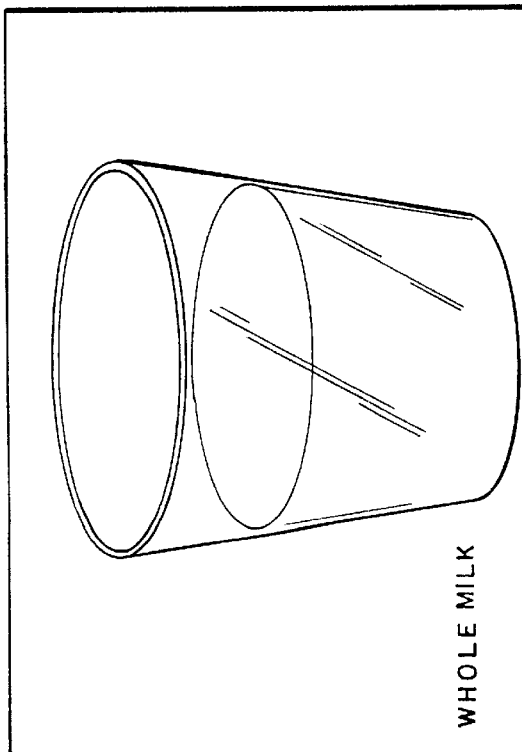
FIG. 2

FIG. 5
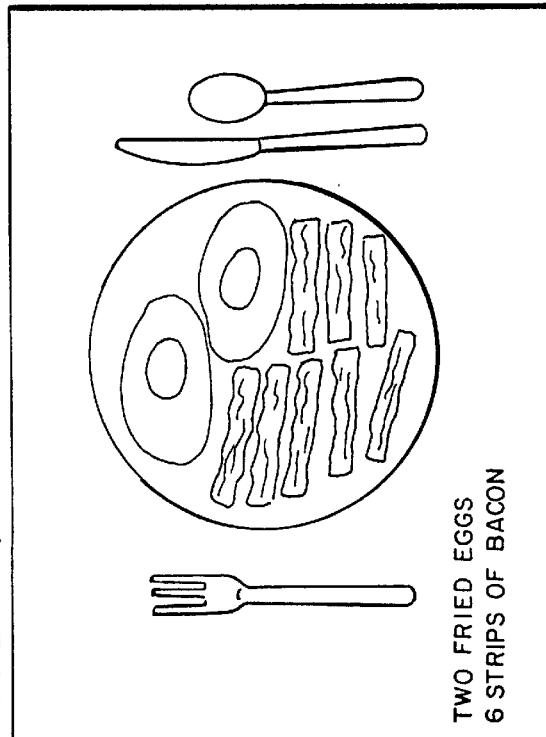
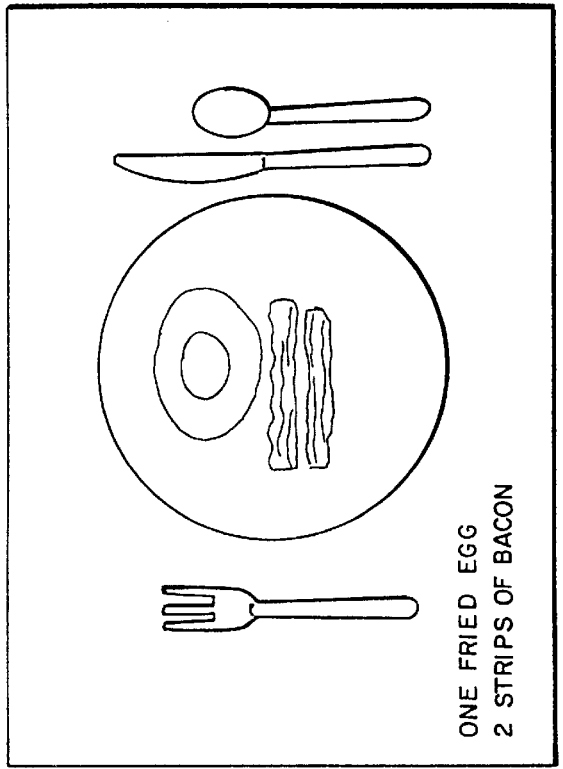

FIG. 14

Diet Behavior Analysis

Choose A    Choose B    Next Screen

Enthusiasm: 1 2 3 4 5 6 7 8 9 10
Frequency: NEVER | SELDOM | SOMETIMES | OFTEN

- Start Eating Behavior
- Preferred Food Frequency
- Food Passion Index
- Your Diet "Fingerprint"
- Consistency Index
- Strengths & Weaknesses
- Visit Library
- Personal Information
- Health Information
- Compare Results With Dietary Guidelines
- Begin Diet Training
- Return to Main Menu
- Internet Club

SYSTEM AND METHOD FOR COMPUTERIZED VISUAL DIET BEHAVIOR ANALYSIS AND TRAINING

This Application is a continuation in part of U.S. application Ser. No. 09/211,392, filed Dec. 14, 1998, currently pending. The disclosure of this patent document, including the drawings, contains material which is subject to copyright protection. The copyright owner has no objections to the facsimile reproduction by anyone of the patent disclosure, as it appears in the Patent and Trademark Office patent files or records, but otherwise reserves all copyright rights whatsoever.

BACKGROUND OF THE INVENTION

1. Field of the Invention

The subject invention relates to the field of behavior analysis and, more specifically, to a computer based method employing visual techniques for analyzing behavior and training individuals to modify behavior. Specific applications include analysis of diet behavior and training of individuals in improved diet practices.

2. Description of Related Art

Present methods of evaluating dietary habits, motivating people to change eating habits, and teaching people how to make healthier food choices are woefully inadequate. Twenty years ago, 20 percent (20%) of Americans were obese. Now 35 percent (35%) of Americans are obese, despite the sales of countless diet books and the increasing availability of low calorie and low fat foods.

Food preferences can profoundly influence the risk of obesity, diabetes, heart disease and cancer. In fact, American dietary habits were responsible for approximately forty percent (40%) of deaths in 1990, and they continue to produce an epidemic of obesity that is out of control.

No effective tools exist for either health professionals or the public that can adequately teach people to understand and immediately recognize the significance of (1) portion sizes; (2) the value and amount of specific macro and micronutrients in different foods; (3) the potentially harmful effects of other naturally occurring substances found in many foods; and (4) the relative quantities of different food choices. Nor are there any teaching tools that can show people how to create meals using food choices that are much more healthful for them and their families. Finally, no teaching or analytical tools exist that use natural visual techniques to assist people to follow diet programs designed by health professionals.

U.S. Pat. No. 5,454,721 to Kuch discloses a system intended to teach individuals the relationship between the visual size and a few nutritional characteristics of portions of food by using either a life size image of, or the corporeal finger of the individual, as a scale against images of different sized portions of different kinds of food, while showing a few nutritional characteristics of such portions. The system proposed by Kuch is limited, in that, for example, it does not evaluate the user's ability to visually estimate macro and micronutrient content of meals. Nor does it permit analysis of an individual's dietary proclivities.

U.S. Pat. No. 5,412,560 to Dennison relates to a method for evaluating and analyzing food choices. The method relies on input by the individual or "user" of food actually consumed by the user during a given period of time and employs a computer program which attempts to estimate the actual intake of nutrients by the individual and to compare that intake to a recommended range of nutrients, such as those contained in dietary guidelines issued nationally in the United States. The approach of the '560 patent is undesirable in that it relies on the individual to provide accurate input data as to his actual food intake, a task as to which there are many known obstacles and impediments, i.e., the approach is not "user friendly." Additionally, no graphic visual displays are provided, which further detracts from ease of use, comprehension and effectiveness.

SUMMARY OF THE INVENTION

The invention comprises a method of computerized behavior analysis. According to the method, a computer database is provided including presentations of a plurality of objects, the presentations being displayable in successive groups, each group including a plurality of presentations. A computer program is then caused to display successive groups, together with display of graphics associated with each of the groups. The graphics are designed to permit a first user selection of one of the presentations of each of the groups, and further user selections related to the presentations selected. The computer is programmed to cause recordation in a storage medium of each of the first and second or further selections so as to generate a database of user choice information from which behavior analysis data is produced. Many applications of this method are disclosed below, a principle one being one wherein pairs of food items and preferences therefor are successively analyzed and a dietary profile produced. Optionally, thereafter, further steps of computerized dietary training may be performed based on the results obtained.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein:

FIG. 2 is a front view of a first computer display according to the preferred embodiment;

FIG. 5 is a front view of a fourth computer display according to the preferred embodiment;

FIG. 14 illustrates an alternative diet behavior analysis screen display;

DETAILED DESCRIPTION OF THE PREFERRED EMBODIMENTS

A principle preferred embodiment of the invention addresses the needs of overweight patients, post cardiac patients, diabetics, and patients with kidney disease and others seeking an improved diet. It employs two programs that complement each other. The first is analytical, while the second teaches new dietary habits.

The analytical program evaluates a person's food choices. These food choices reveal innate preferences which have profound health implications. For example, in a way analogous to choosing foods at a buffet, the analytical program may reveal a preference for fatty foods, a dislike of vegetables, a preference for red meat, a tendency to choose large portions, and so on. This analytical evaluation uses high-resolution photographs of foods and meals that mimic choosing foods in real life situations. The program design enables the food database to be modified or replaced with new or alternative food databases, such as those that reflect ethnic diversity or specific medical needs.

The training program adapts to the results of the analytical program. After the goals are established, the training program displays an empty plate on the screen. Foods are then selected from scrolling photographs on the side of the screen and, using click and drag or other means, are placed on the plate before portion sizes are adjusted by either increasing or decreasing the actual size of the image or by increasing or decreasing the number of images of the same size. The meals that have been "created by eye" are then evaluated against the new diet goals.

Alternatively, the user is challenged to evaluate the nutritional balance and content of a series of foods or complete meals that are generated by the program. This could, for example, be by the answering of multiple choice questions, which might be followed by the option to modify the appearance of the meal by changing the amount of any one or more of the foods on the plate, and even by substituting foods from a pop-up list of alternatives.

The ultimate success of this system is that an individual can really be made to understand the strengths and weaknesses of their present dietary habits, and they can recognize by sight what meals of the optimum dietary balance for the set dietary goals look like without counting calories or grams of fat. In addition to teaching visual recognition, users can also be provided, if desired, with access to a library of information, visit a virtual supermarket, select recipes, obtain health tips, get detailed nutrient analysis, etc.

Figure 1:
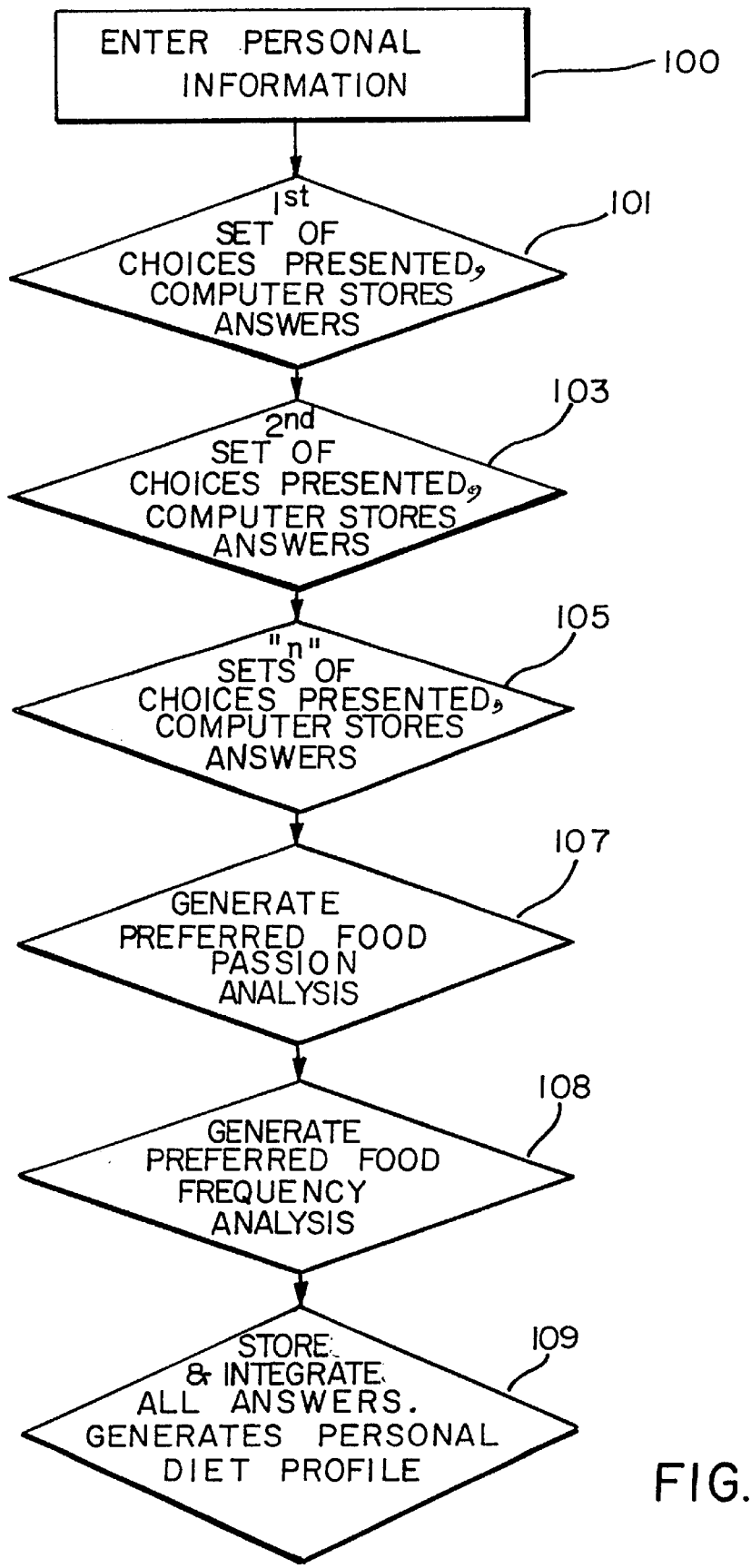
FIG. 1 is a flowchart illustrating a routine for computerized dietary behavior analysis according to the preferred embodiment.

A flowchart illustrating a diet behavior analysis program according to the preferred embodiment is shown in FIG. 1. As illustrated in steps 101–105 of FIG. 1, the algorithm successively selects "n" pairs of food items or "objects" from a computer database based on predetermined criteria, including nutritional criteria, portion size and ethnic variations. A food object may consist of a single food item such as a glass of milk or may comprise multiple items, such as "bacon and eggs."

In this example, pairs of food objects are presented, i.e., displayed, to the user who then inputs and records a choice of one of each pair of food objects presented on the computer screen, and indicates his or her level of enthusiasm and desired frequency of consumption of both items. The level of enthusiasm and desired frequency of consumption is indicated by user interaction with corresponding graphics presented on the display. Such interaction may be achieved by various conventional means, such as "mouse" selection.

The program, according to FIG. 1, further monitors and stores the user's selection, level of enthusiasm and desired frequency of consumption. Every user choice is evaluated for calories, fat, fiber, portion size and a range of macro and micronutrients. Macronutrients include protein, various types of fats, various types of carbohydrates, including dietary fibers. There are numerous micronutrients that include: Vitamins A, B group, folic acid, C, D, E, carotenoids, etc and minerals including, for example, calcium, magnesium, selenium, zinc, etc.

Each food selection from paired (or multiple) images provides an indication of the innate liking for the item displayed, and since each individual food item or meal has nutritional characteristics that are distinctive, the program provides an accumulation of information that reflects the degree of liking for foods with those characteristics. Consequently, by way of example, if the user chooses the high fat rather than the low fat option 15 times out of 20, then evidence has been gathered that the user generally prefers the taste of fat and fatty foods. If this trend is also supported by a preference for larger portions 8 times out of 10, when offered high fat options, but only 2 times out of 10 when offered low fat options, then this result further confirms that the user is likely to consume fat in excess in the future. This information can be further refined by the program to provide actual analyses of accumulated choices when they are structured into an eating pattern typical of daily consumption: namely, breakfast, lunch and dinner. Such accumulated choice analysis, then, provides an estimate of the total daily consumption of macronutrients and micronutrients, which, when repeated, can provide estimates of average weekly or even monthly consumption.

The progressively accumulated record of food choices may then be interpreted quantitatively by matching these choices with a nutritional numerical database. This interpretation provides an indication of how the user's choices affect average prospective consumption of macro and micronutrients.

The above described operation may be illustrated in further detail with reference to examples of specific steps of FIG. 1, illustrated in FIGS. 2–5. In the case of the computer screen shown in FIG. 2, for example, the user's choice primarily indicates animal fat preference or avoidance. The enthusiasm and frequency factors have long term health implications. In every case the answer is stored and combined with answers to subsequent choices.

Figure 3:
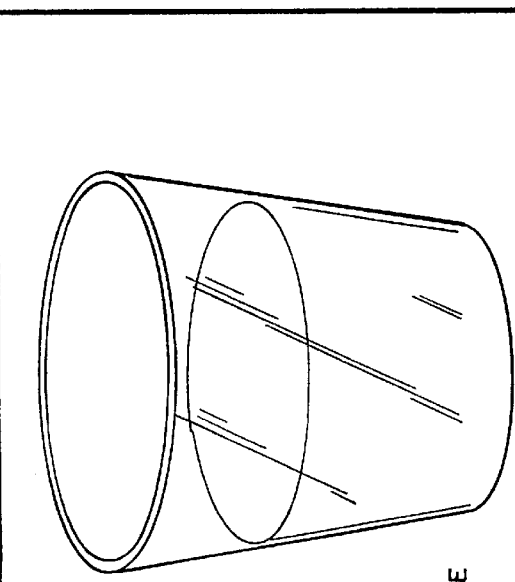
FIG. 3 is a front view of a second computer display according to the preferred embodiment.

For example, the next choice might be that illustrated in FIG. 3. This choice has implications for the intake of protective vitamin C, folic acid and other phytonutrients such as limonene in orange juice, compared to harmful fat and useful vitamin D and calcium in milk. Again, anticipated frequency and hence quantity is important for long term health effects.

Figure 4:
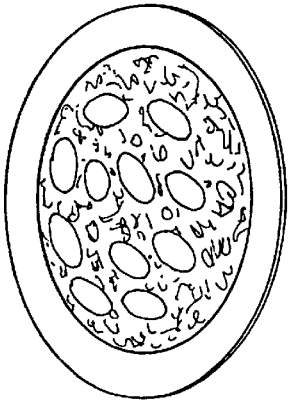
FIG. 4 is a front view of a third computer display according to the preferred embodiment.

FIG. 4 presents a choice of breakfast cereal. In this instance, both choices provide a good choice of cereal fiber, but the addition of a banana adds a significant nutritional benefit. It also implies a liking for fruit and an inclination to include fruit in the diet. An increased fruit intake and an increase in fiber are associated with a lower risk of some cancers and heart disease.

FIG. 5 presents a choice to a person who is offered fried eggs and bacon for breakfast. This choice has significant health implications. Fried foods are high in calories and high in fat content, and the fat is usually the more harmful saturated fat. The American Heart Association recommends a daily cholesterol intake of less than 300 mg per day (one egg has 265 mg). The meal on the left provides 38 grams of fat. The one on the right has 18 grams of fat. Clearly, choosing the larger portion size dramatically increased fat and cholesterol intake, and provided double the calories. This suggests habits that are likely to increase risks of obesity, heart disease and certain cancers.

After responding to, for example, 300 paired food choices (i.e., "n"=300) at steps 105, of FIG. 1, the program then analyzes the selections based on specific criteria. The Behavior Analysis is thus based upon answers to paired or multiple choices being grouped in categories that will indicate enthusiasm and frequency for macronutrients such as fat, protein, simple and complex carbohydrates, dietary fibers, portion sizes, total calories, etc. These data are averaged as they accumulate until at the end of the analysis, in step 109, of FIG. 1, answers to questions about any of the key criteria are summarized in a final graphically displayable report, which may be termed a Personal Diet Preference Profile.

Figure 6:
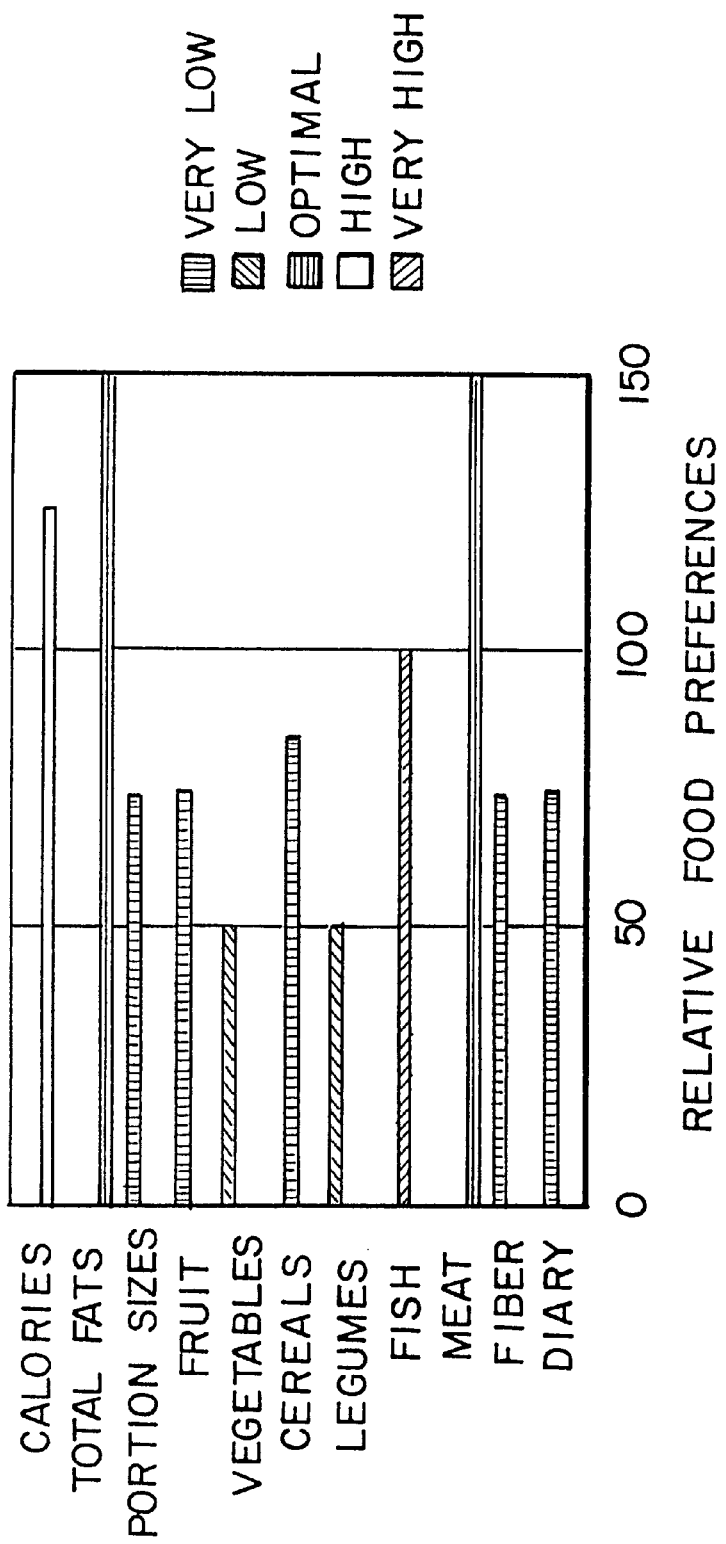
FIG. 6 is a display of a personal diet profile according to the preferred embodiment.

An example of a diet profile or "fingerprint" is shown in FIG. 6. As may be seen, the display is a simple horizontal bar chart, scaled for example 0, 50, 100 and 150. The bars are each colored with a respective different color to further indicate whether the preferences range from very low to very high. For example, "very high" may be the color "red" to particularly flag the excessive meat and fat preferences reflected by the profile shown in FIG. 6. FIG. 6 thus represents a type of diet "fingerprint," which reflects integrated food choices with both the instinctive level of enthusiasm and the instinctive preferred frequency.

The line numbers 50, 100, 150 in FIG. 6 indicate a relative scale that is roughly equivalent to a percentage scale. The number 100 represents the typical or generally recommended dietary intake of a specific ingredient (or calorie intake), with deviations above or below being expressed in relative terms. It assumes an "average" level of enthusiasm. If enthusiasm (passion) is higher or lower than average, and if instinctive desired frequency is higher or lower than average, these two components are integrated by the program algorithm to provide a final impression of predicted food consumption.

The behavioral analysis provided need not be extremely precise. Rather, it is sufficient to provide the user with an indication of strengths and weaknesses in his or her diet that will provide two advantages: first, it will motivate the user to want to make adjustments in their dietary habits; second, it provides the software program with an indication of food and taste preferences that can be incorporated into the final design of a new diet plan, or new diet goals—even when based upon official dietary guidelines such as those published by professional associations.

Figure 7:
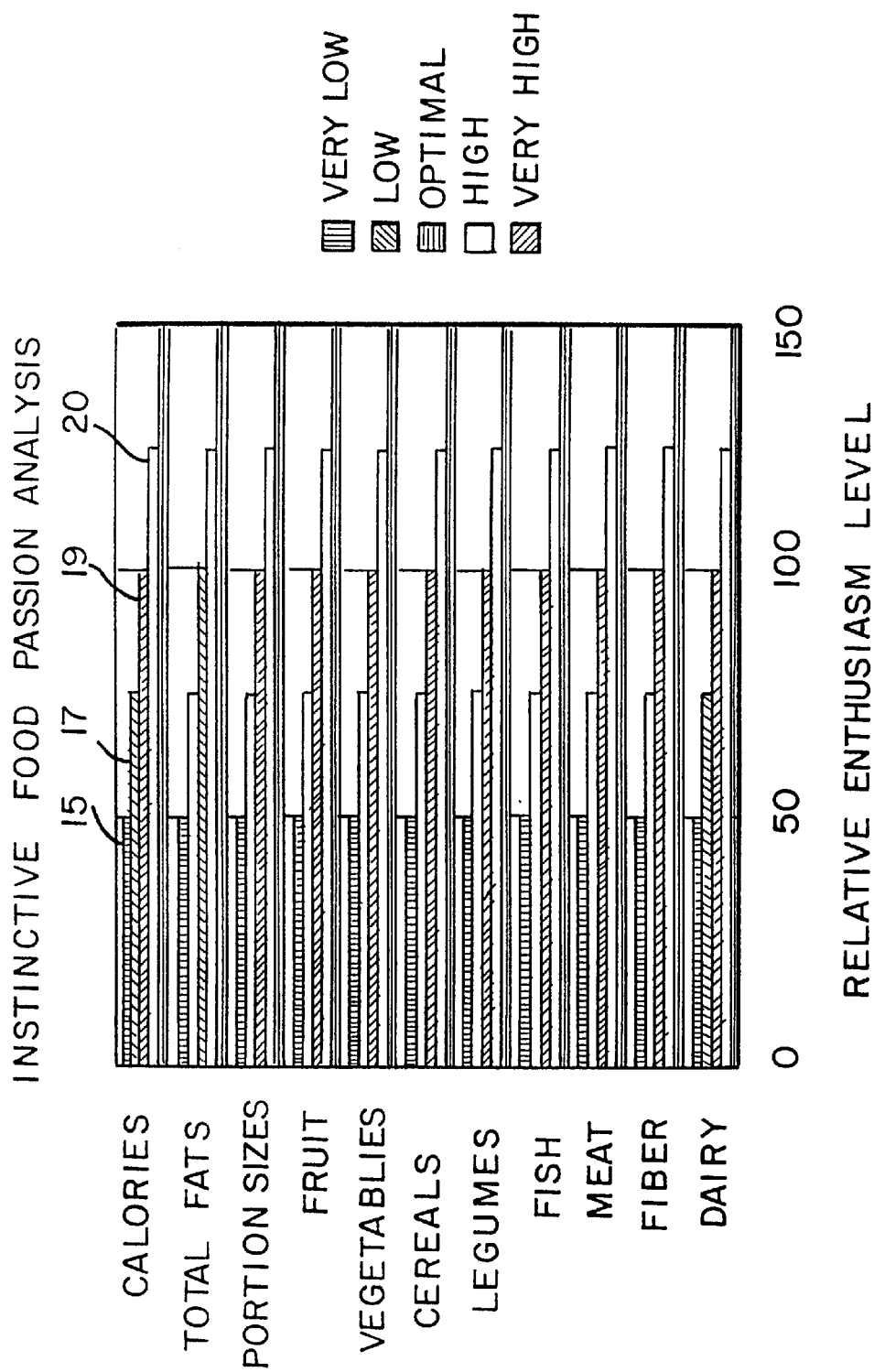
FIG. 7 is a display of an instinctive food passion analysis according to the preferred embodiment.

Preferably, to increase understanding a separate analysis is made (step 107, of FIG. 1) of the enthusiasm with which choices are made and the enthusiasm (or lack of enthusiasm) expressed for choices that were rejected. Such an analysis may be termed an Instinctive Food Passion Analysis. An example of a food passion analysis screen display is shown in FIG. 7.

As will be appreciated, "Passion" is simply a catchy word for level of enthusiasm. The level selection is entered into the personal record database of the user as the user reviews all of the objects, i.e., food or meal choices, offered during the behavior analysis steps. The level selection is preferably made on a scale of 1 to 10, and values are recorded and averaged for each diet category. FIG. 7 presents "passion" as one of four horizontal bars, e.g., 15, 17, 19, 21, for each of a number of pertinent dietary measurement categories, e.g., calories, total fats, portion sizes, fruit, etc. Color-coding is again preferably used to enhance user understanding and retention.

Figure 8:
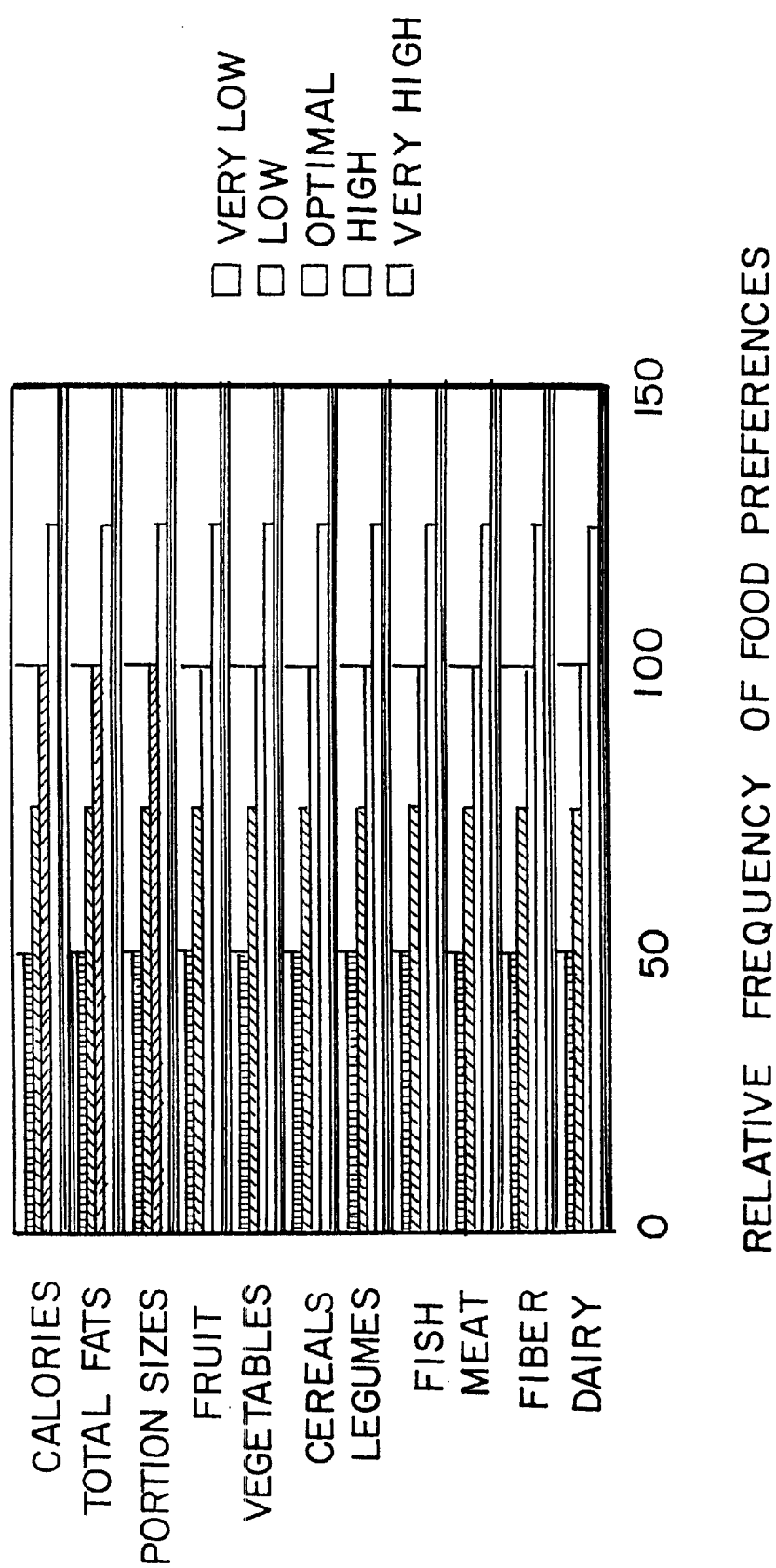
FIG. 8 is a display of an instinctive food frequency analysis according to the preferred embodiment.

Additionally, the user is preferably shown an Instinctive Food Frequency Analysis generated at step 107, of FIG. 1. This analysis reveals his or her natural tendency to desire certain foods either more or less often. An example of a food frequency analysis screen display is shown in FIG. 8. FIG. 8 employs the same four bar, color-coded display techniques shown in FIG. 7, but this time graphs "relative frequency" on the horizontal axis as opposed to "relative enthusiasm level."

Figure 9:
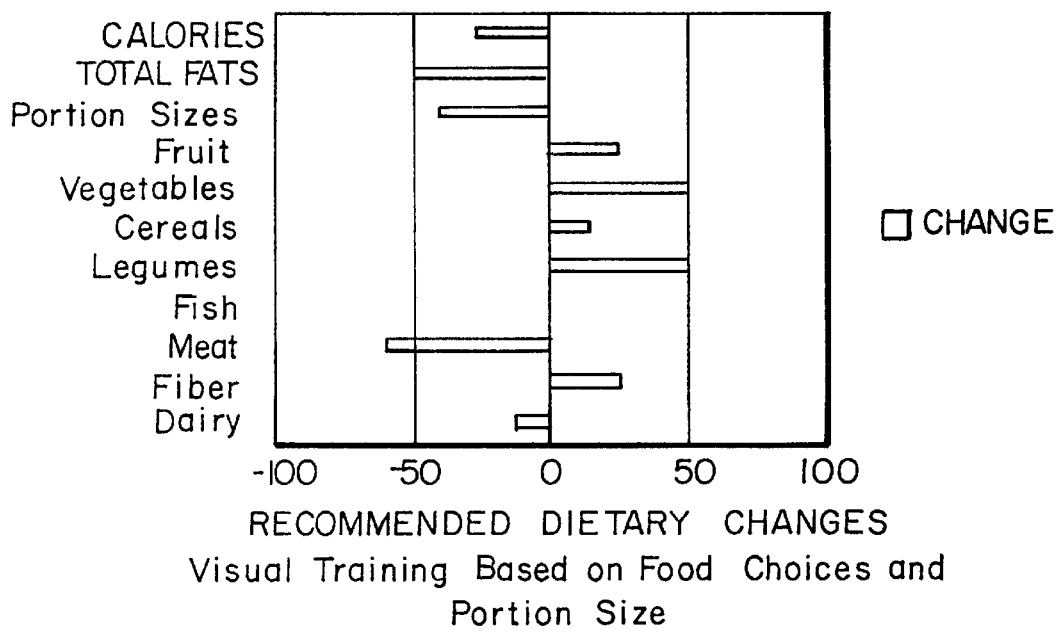
FIG. 9 is a display of recommended dietary changes.

Based on the data collected according to procedures such as those illustrated in FIGS. 1–8, recommended changes in food intake and frequency in order to achieve new dietary goals may be prescribed by a nutritionist or dietitian, physician or other health professional, or by the subject when using a personal version of the software. FIG. 9 is an exemplary illustrative screen display which reflects needs to change food choices, frequency and portion sizes. On this display, "optimal" intake of various categories, such as calories, total fats, etc. is represented by "100" on the horizontal axis. Aside from the collection shown in FIGS. 6–9, the parameters computed and displayed can comprise: total calories, total fats, calcium, cholesterol, dietary fiber, and antioxidants. Color-coding is again utilized for further emphasis.

Thus, FIG. 9 represents the adjustment needed to bring all of the bars in FIG. 6 back to the 100 (correct) position. This change in relative consumption of different food categories is preferably incorporated into a diet plan which represents the new dietary goals of the user. This plan is built on goals that are either generated by the computer to conform to nationally established dietary objectives, or to dietary goals that are designed by a health professional or possibly imposed by the user.

At this stage, the professional dietitian, nutritionist or physician can discuss the patient's dietary habits and their implications for weight control, specific medical conditions, or long term health. The Diet Behavior Analysis, together with the separate Instinctive Food Passion Analysis and Instinctive Food Frequency Analysis, may then be used to motivate the patient to make essential changes in their dietary habits. This approach is analogous to the use of elevated blood pressure or serum cholesterol to motivate people to take corrective action. The health professional can also establish dietary goals based upon this analysis with the help of the computer. The health professional can retain the ability to override the computer-generated recommendations at any time.

Once the diet goals have been defined, the patient begins visual diet training. Visual training is designed to enable the patient to recognize at a glance what their new diet should look like. Visual training is accomplished by user interaction via the computer with a series of virtual meals.

PHASE 2. Visual Diet Training

As discussed above, upon completion of the Diet Behavior Analysis, the patient receives a Diet Report, e.g., FIG. 9, that is designed to highlight the strengths and weaknesses of their instinctive dietary habits. This analysis is then used to design new dietary goals and increase motivation, which is used in the Diet Training Program that follows. These dietary goals may be designed as far as possible to include foods that have been identified as "preferred foods" by procedures leading to generation of FIG. 7 of the Diet Behavior Analysis.

The presently preferred dietary training shows the user meals and foods that look as real as possible. The computer program provides the ability to create partial or full meals, adjust portion sizes, discover the nutritional contribution of each component of the meal or each food item selected, assess the final nutritional content of the whole meal, and accumulate this information as a series of meals are created. At any point in the process, the patient can measure their skill in selecting a proper meal by comparing their new dietary balance with the goals that have been set by the computer or the dietitian or physician. At any stage, the capability may be provided to access a "Virtual Library" to learn about diet and nutrition. If the patient needs help, the computer can be asked to redesign or adjust the meals to match dietary goals. It can also help to create shopping lists that match dietary goals.

Figure 10:
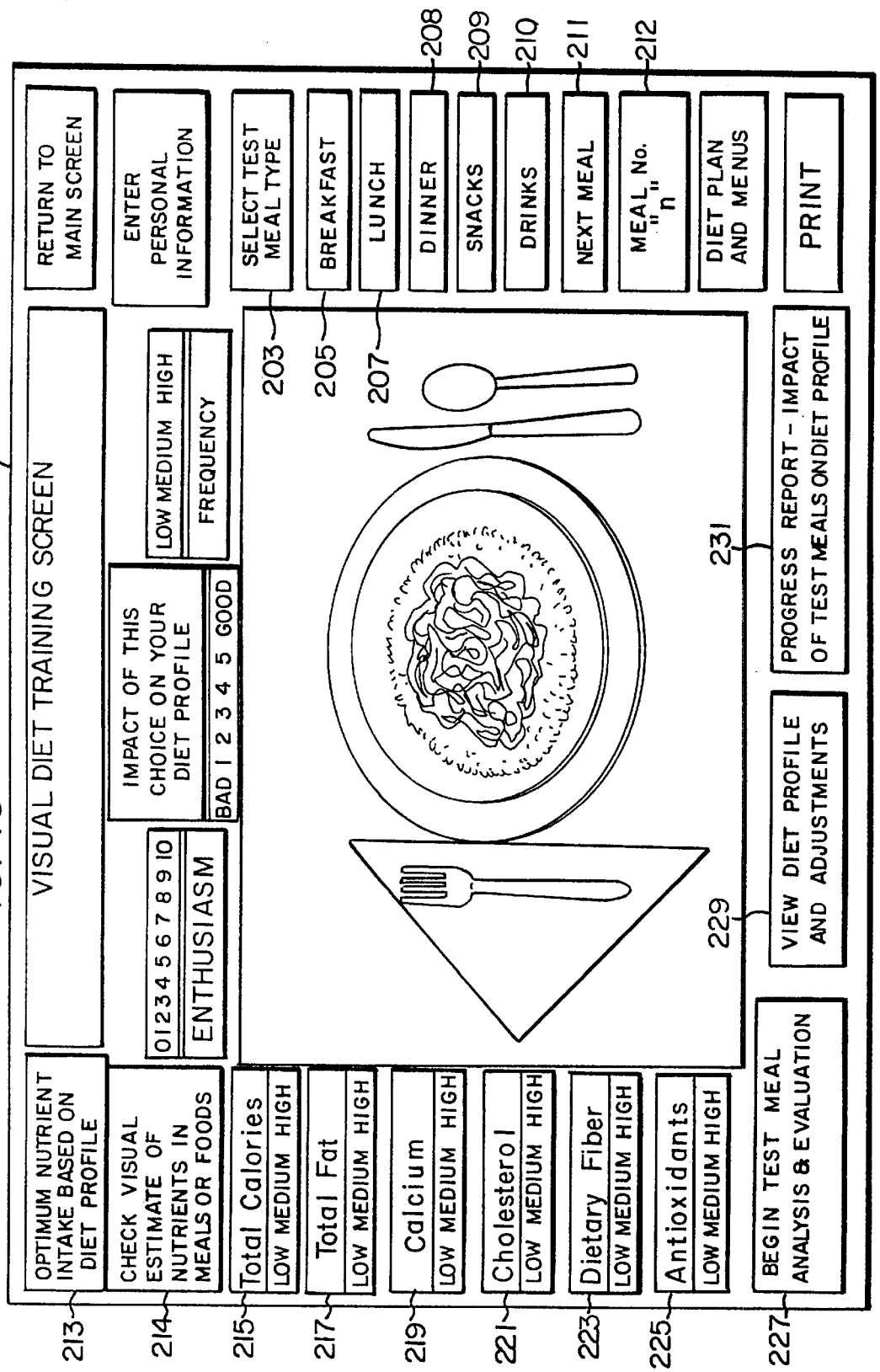
FIG. 10 is a front view of a first diet training screen display according to the preferred embodiment.

A first approach to dietary training is illustrated in conjunction with FIG. 10. The computer display screen 201 of FIG. 10 includes a number of mouse-selectable items or icons. On the right hand side of the screen, icons 205, 207, 208, 209, 210 permit the user to select a test meal type, i.e., breakfast, lunch, dinner, snacks and drinks. In response to selection of breakfast, for example, the computer presents the user with a plate including various selected breakfast food items. On the left side of the screen 201 are icons 215, 217, 219, 221, 223 and 225, which permit the user to estimate the nutrient content of the meal for various nutrient-related parameters. In the case of FIG. 10, the parameters are total calories, total fat, calcium, cholesterol, dietary fiber and antioxidants but these parameters may vary depending on the given application. Thus, the user is called upon to estimate whether the meal presented is "low," "medium" or "high" in content of these various parameters. In other embodiments, such measurements may be more detailed or precise.

In the upper left corner of the display 201 are icons 213, 214 labeled "Optimum Nutrient Intake Based on Diet Profile" and "Check Visual Estimates of Nutrients In Meals or Foods." Selection of these icons results in the opening up of separate screens: one that reveals details of individual nutrient/food adjustments which will improve the user's diet profile; and another screen that checks visual ability to estimate nutrient content of sample foods or meals. This latter screen provides a comparison of the user's estimates, e.g., "low," "medium" or "high" to the correct estimate. The former may be a screen displaying information such as is shown in FIG. 9.

Figure 11:
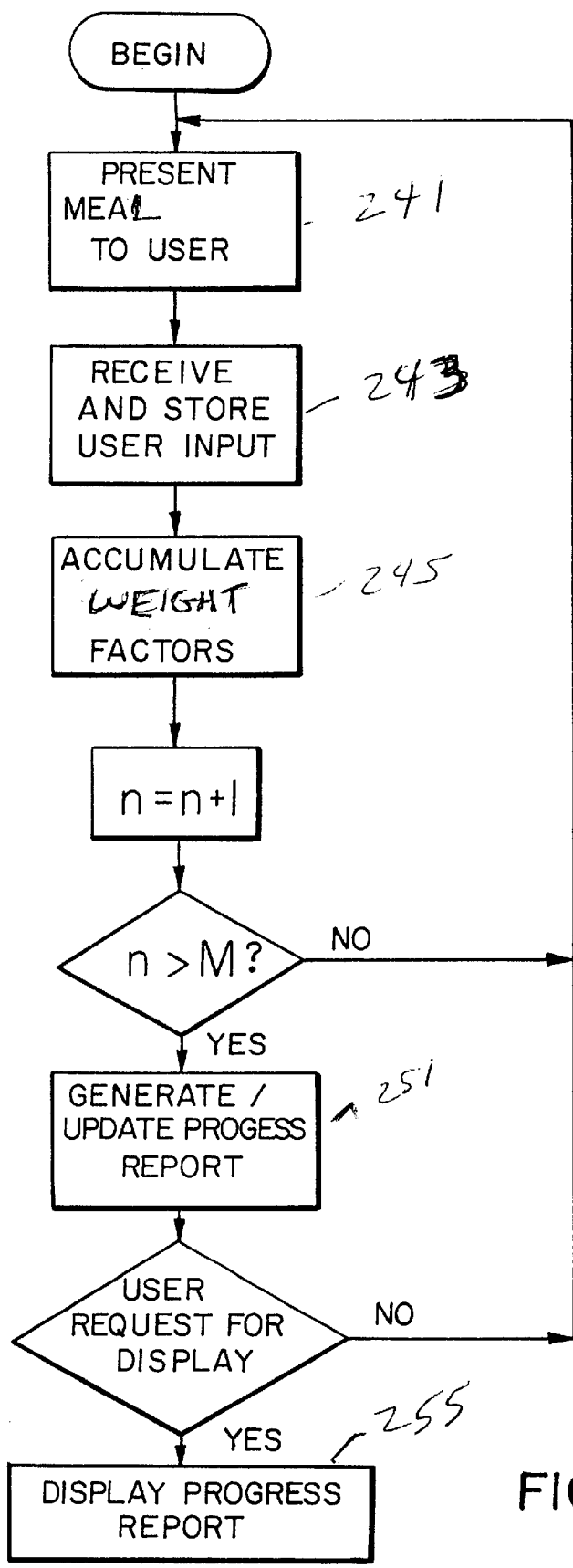
FIG. 11 is a flowchart illustrating computer programming facilitating use of the screen display of FIG. 10.

The programming and operation of a digital computer facilitating use of the display of FIG. 10 is illustrated in the flowchart of FIG. 11. Initially, the user clicks on the "Begin" icon 227, the "Select" icon 203, and one of the particular meal icons 205, 207, 208, 209, 210. In response, in step 241 of FIG. 11, the computer causes display of an appropriate meal. Then the computer receives and stores the user's "low," "medium," or "high" selection as to each nutrient-related parameter item, step 243. A numeric weight is attached to each selection such as "10" for the least correct, "20" for closer to correct, and "30" for the most correct answer. In step 245, the value of each of the weights is accumulated, i.e., added to the value of the previous weight parameters stored for each of the prior meals.

After "n" meals are presented, a progress report is generated, step 251. For example, "n" can be zero, in which case the progress report displays a comparison of the total weights selected by the user to the maximum total weights achievable, i.e., 6×30=180 for the six parameters displayed in FIG. 10. If the user clicks on the "progress report" icon 231, the program responds in step 255 by displaying the comparison.

The user may then continue to practice on additional meals in order to improve his program diet estimating capabilities. In another mode of operation, "n" can be greater than zero, and more complicated algorithms can be used, such as accumulation of results over ten meals, as opposed to one. Alternatively, the computer may also display the correct answers after each of the respective six meal selection icons is touched. The alternative modes can all be available and the particular mode selected by the user, e.g., by a conventional drop down menu provided on the display.

The embodiment of FIGS. 10 and 11 thereby provide the user with feedback as to his or her ability to judge the nutrient content of a series of food items and develops the ability to select foods based on their nutrient content and their concomitant impact on a personal diet profile. It will be appreciated that with appropriate programming, the user can be shown how one or more meal selections contribute, individually or cumulatively, to the attainment of the defined dietary goals. This progress is typically displayed as a bar chart that compares the starting point (how much adjustment is needed) to the cumulative impact of the choices that have been made. This enables the user to see immediately how close he or she is to achieving the dietary goals, and how much more needs to be done to reach them.

Figure 12:
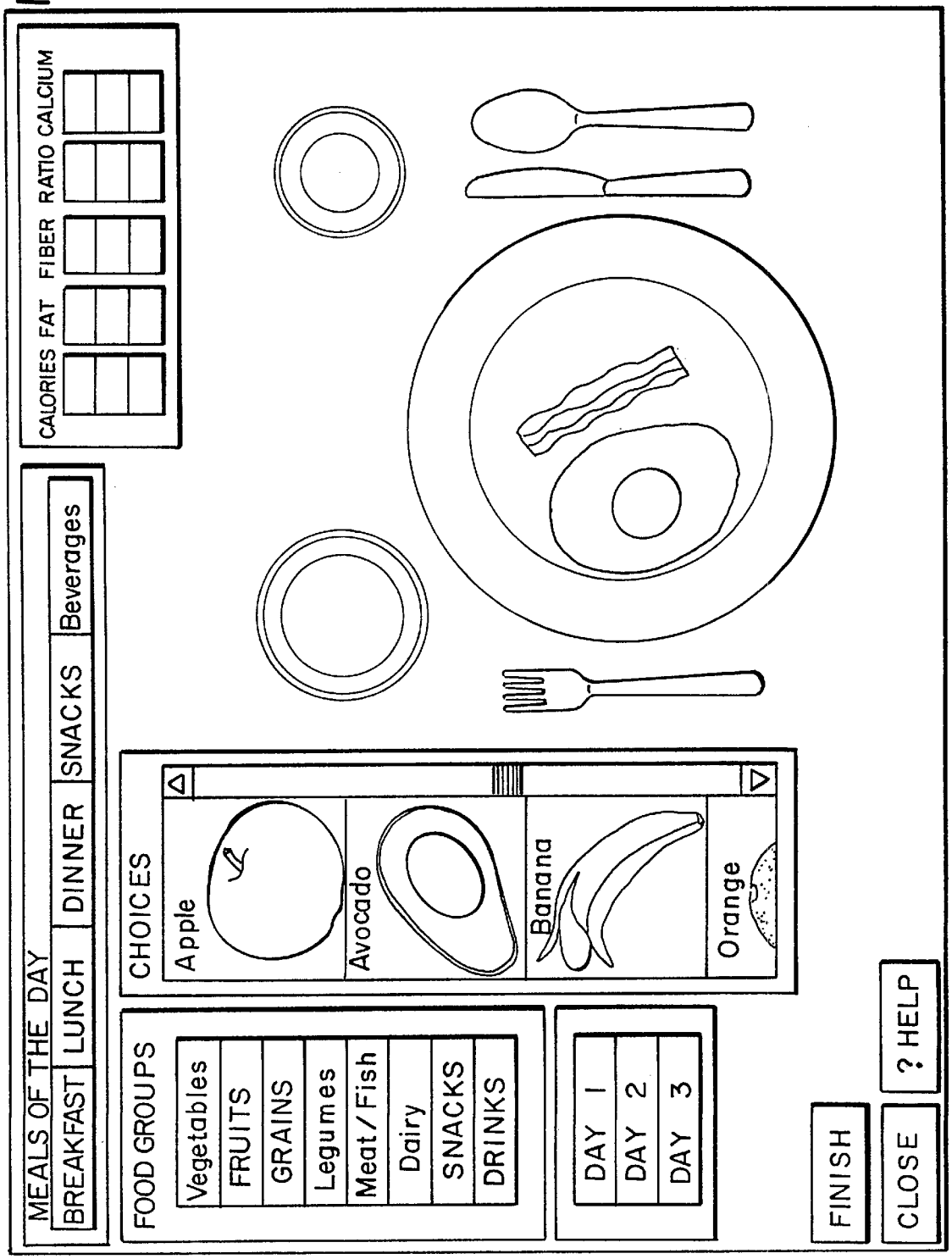
FIG. 12 is a front view of a first diet training screen display according to the preferred embodiment.

Diet training according to a second approach is based upon the visual creation of meals from food lists or photos presented as optional choices on the side of the screen, e.g., as shown in FIG. 12. The user first selects a meal type by clicking on an appropriate icon. In response, the program displays a selection of food. Items are then moved onto an empty plate as realistic food images, for example, by 'click and drag'. Portion sizes may be adjusted by clicking on a + or − sign. The user clicks on an icon to indicate that meal creation is complete and on another icon to begin creation of another meal. Hence a virtual meal is created.

Figure 15:
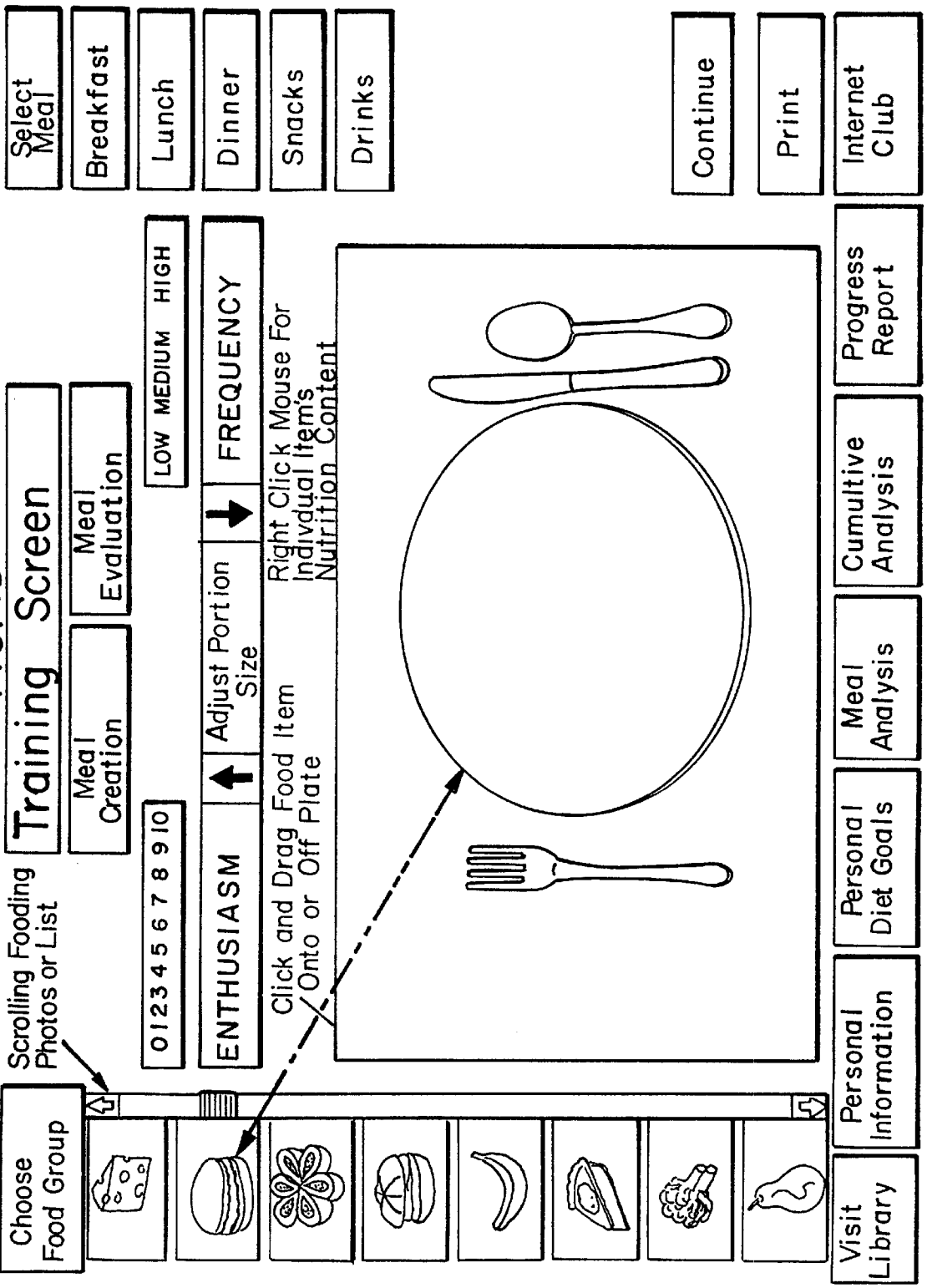
FIGS. 15 and 16 illustrate alternate embodiments of meal evaluation and creation screens, respectively.
Figure 16:
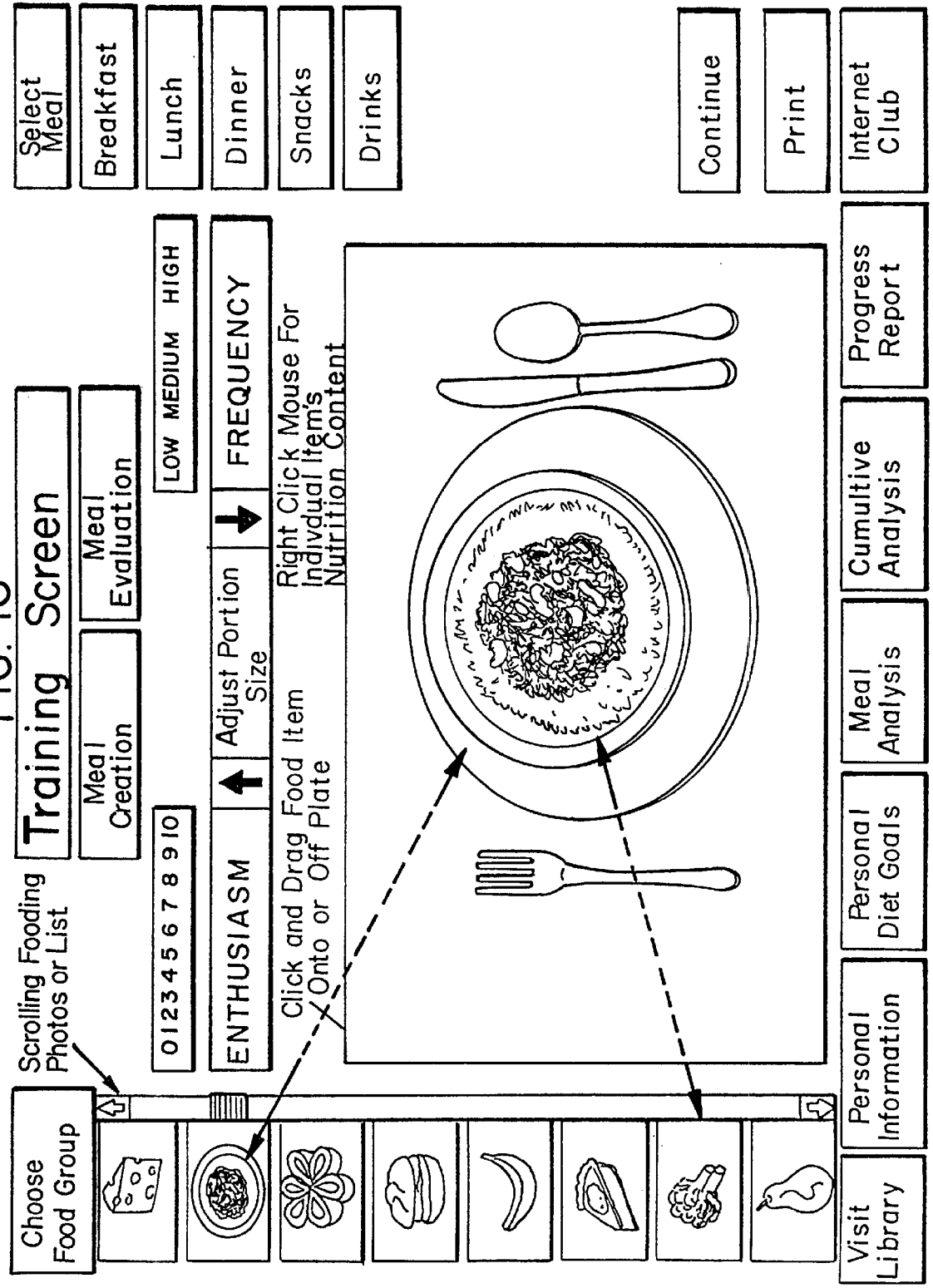

As an example, food selection and portion size adjustment may be engaged-in with the main goals of achieving consumption of no more than 50 grams of fat, at least 45 grams of protein and a selected percentage of fiber, per day. Fat intake is specified to achieve a desired ratio of saturated, more saturated and polysaturated fats, as well as other fats. By interaction with the computer display, e.g., of FIGS. 12, 15 and 16, the user can tell whether his or her meal (or food item) selection is within the defined goals and/or likely to cause daily intake to exceed the desired goals. Additional meals are then created, adjusted and evaluated, and then cumulative dietary contributions are compared against the desired daily goal.

Figure 13:
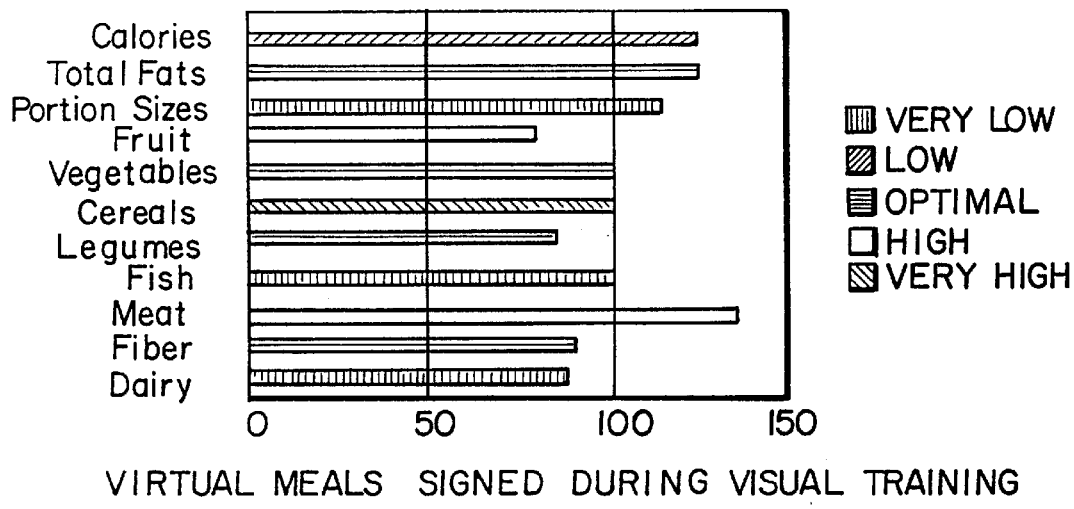
FIG. 13 is a display illustrating progress achieved by training according to the preferred embodiment.

Progress in meeting dietary goals is preferably also displayed graphically. After a period of training that can be varied to suit the individual patient, the results of an illustrative follow-up analysis might look like that shown in FIG. 13. Clearly, in this example, the patient has shown an enhanced ability to recognize the right food choices with a better sense of frequency, while not yet reaching the dietary goals that were set following the initial analysis.

A significant advantage of the preferred dietary training embodiment is the fact that the patient or user is being trained without the patient being encumbered by detailed numerical instructions, detailed diet plans and other mathematical challenges that greatly discourage anyone from sticking to rigid diets. Exceptions to this, of course, will occur when specialized medical needs are being addressed, such as in patients with renal disease.

Figure 17:
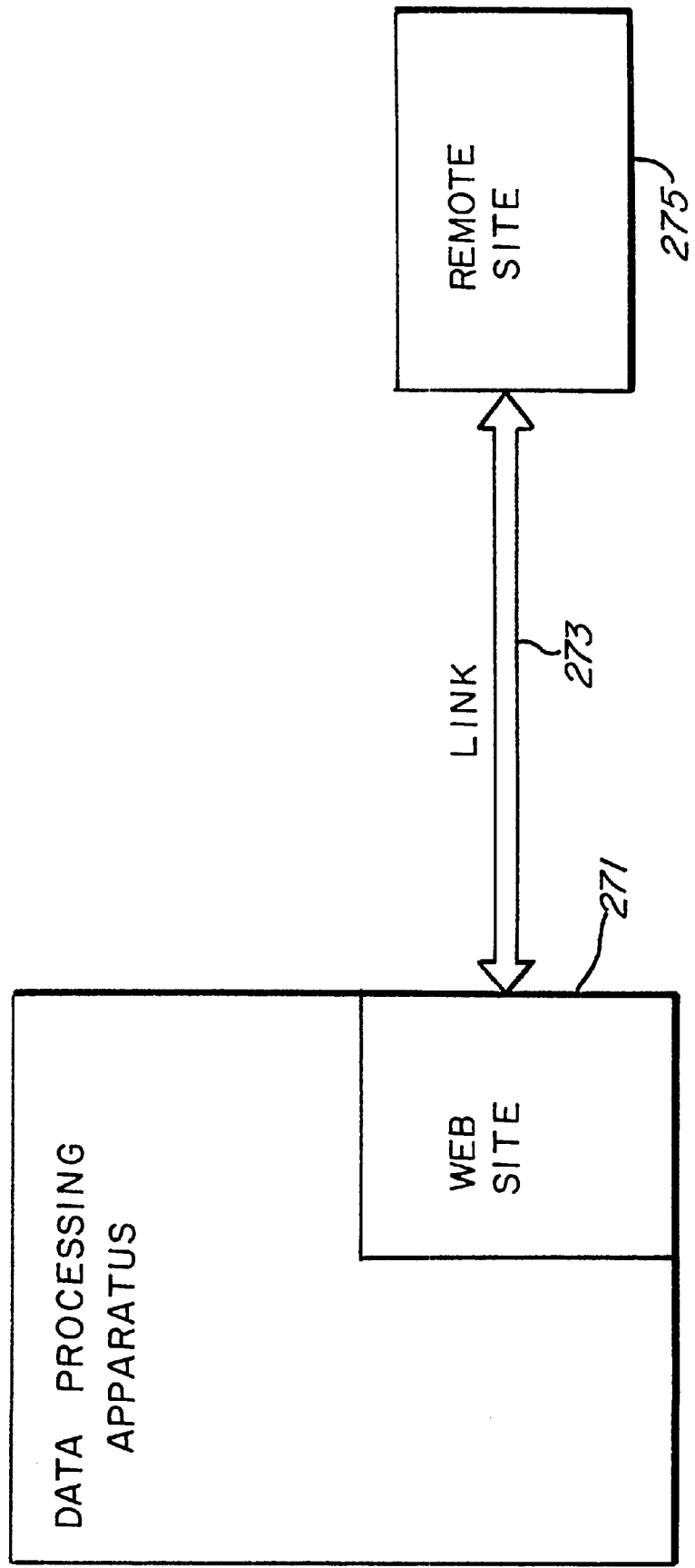
FIG. 17 illustrates apparatus useful in one implementation of the preferred embodiment.

The dietary evaluation and training methods according to the preferred embodiment are advantageously made available at a website where they may be accessed over the Internet by home personal computers and other remote terminals or sites. FIG. 17 illustrates a system wherein a website 271 supplies access to the interactive processes and displays illustrated herein over a communication link 273 to a remote site 275. The communication link 273 may be connected to one or more home personal computers, professional site computers or various other data processing apparatus which provides display and user interaction with interactive and graphical displays as disclosed above. The communication link may comprise the internet or various other transmission paths providing two-way communication of data between the website 271 and various remote terminals. The website 271 is set up as a conventional website located, for example, on a conventional server or other data processing apparatus.

Other Applications of the Invention

It may be observed that the method of the preferred embodiment can be applied in many behavioral analysis and modification contexts. Thus, database modules may relate to health, lifestyle, commercial or other behavior analyses. In general, one may provide Exchangeable Database Modules of paired or multiple photographs, drawings or descriptions of any objects, which interact with a software algorithm. The computer program or algorithm selects "n" pairs or other multiples of objects based on specific criteria, including size, shape, color, texture or other identifying or functional variations. The user then inputs and records choice of one of each pair or more presented on screen, and indicates level of enthusiasm and desired frequency of consumption or utilization of both or all items. Interactive software algorithms then utilizes the user input data and integrates such data with predetermined or derived criteria to create a plan for behavior modification that can be manually overridden and then evaluated.

Behavior Modification Training depends upon the virtual assembly of objects based upon visual, physical or chemical or functional criteria or other descriptors presented as optional choices on the computer monitor. Chosen items can be identified and moved onto any virtual surface, platform, table, or plate as realistic images by 'click and drag' or other means. Physical, chemical, visual or functional characteristics may be modified by the user. Alternatively, computer-generated objects, or object combinations selected from external but linked exchangeable database modules, are presented either randomly or selected for visual evaluation of physical or chemical, or other characteristics. Objects can then be modified selectively by changing physical, chemical or visual characteristics.

Other applications where the invention is applicable include the following:

Market Research

Analyzing and recording individual or collective preferences between paired or multiple choices of objects and/or images stored in a database that differ in shape, color, design, form or other physico-chemical characteristics; or from a database of comparative texts. (e.g. different insurance policies.)

The database may be stored on CD-ROM, on DVD, on the computer's hard drive, or it may be stored on a remote internet based server.

Analyzing specific characteristics of individual or collective choices.

Determining preference profiles among specific individuals, populations or consumer groups.

Design or Product Modification

Based on results from the initial analysis, modifications in product appearance, design, functionality or other characteristics are made and then again re-evaluated among target consumer/population groups.

Alternatively, selected images of products, concepts or services are presented with options for consumer selected modification. This would provide insight into customer preference that can be incorporated into the redesign of products, concepts or services that more closely match consumer needs.

Graphic Output of Results of Behavior or Preference Analysis

Based upon revealed preferences, attempts are made by the program to impose different characteristics on the "objects" or data in the database.

Then, the degree to which these imposed changes are accepted or continually rejected by the target individual or group is measured and re-evaluated.

Areas of use of the invention include: Architectural Design/Sales, Interior Design/Sales, Furniture Design/Sales, Product Design/Sales, Fashion Design/Sales, Selling Real Estate/Sales, Menu Design, Food Design (such as formulating and presenting a packaged food or meal), Packaging Design, Car Design/Sales, Boat Design/Sales or Health or Life Insurance policy selection.

Those skilled in the art will recognize that methods according to the invention may be readily practiced in conjunction with conventionally known hardware, such as personal computers, which may include a microprocessor and associated read-only and random access memory, as well as accompanying CD-ROM, CD-ROM or DVD drives, hard disk storage, or other storage media, video memory, mouse, keyboard, microfiche sound I/O, monitors and other such peripheral devices. Multiple terminal embodiments may be configured for clinical use utilizing a computer server and a plurality of video terminals for a plurality of patient/users.

Those skilled in the art will further appreciate that various adaptations and modifications of the just-described preferred embodiments can be configured without departing from the scope and spirit of the invention. Many different display screen and format embodiments can be utilized, a number of which are illustrated in FIGS. 2–14. Therefore, it is to be understood that within the scope of the appended claims, the invention may be practiced other than as specifically described herein.

What is claimed is:

1. A method of computerized diet training comprising the steps of:

completing a diet behavior analysis, where the diet behavior analysis comprises collecting and analyzing specific information on a user's instinctive eating tendencies and preferences;

providing a computer database based on the diet behavior analysis comprising one or more food items;

displaying one or more groups of food items to a user;

each group including one or more food items; and displaying a nutrient-related parameter of at least one group to the user.

2. The method of claim 1, wherein the nutrient-related parameter is the number of calories associated with the at least one group.

3. The method of claim 1, wherein the food items are displayed graphically.

4. The method of claim 1, wherein the groups are displayed on separate plates.

5. A method of computerized diet behavior analysis, where the diet behavior analysis comprises collecting and providing specific comparative information on a user's instinctive eating tendencies and preferences, comprising the steps of:

storing in digital format images of first and second groups of food items, each group including one or more food items;

displaying the first and second groups adjacent to one another on a viewing screen; and reacting to said groups by indicating at least one parameter selected from the group consisting of preferred consumption, frequency of consumption, and preferred amount.

6. The method of claim 5 wherein the viewing screen is a computer display screen.

7. The method of claim 5 wherein said images are stored at a website and wherein said method includes the further step of transmitting said images over the internet to said viewing screen.

8. The method of claim 7 further including the steps of point-and-click selecting an indication of the reaction to said images of a viewer of said images.

9. The method of claim 8 wherein said reaction is a selection based upon a comparison of said images.

10. A method of computerized diet behavior analysis, where the diet behavior analysis comprises collecting and analyzing specific information on a user's instinctive eating tendencies and preferences and comparing the specific information to a set of diet goals, comprising the steps of:

storing in digital format images of first and second groups of food items, each group including one or more food items;

displaying the first and second groups adjacent one another on a viewing screen; and reacting to said groups by indicating at least one parameter selected from the group consisting of preferred consumption, frequency of consumption, or preferred amount.

11. A method of computerized diet behavior analysis, where the diet behavior analysis comprises collecting and analyzing specific information on a user's instinctive eating tendencies and preferences, comprising the steps of:

providing a computer database including presentations of one or more objects, said presentations being displayable in one or more successive groups, each group including one or more said presentations;

causing a computer to display the one or more successive groups, together with display of graphics associated with each said group, said graphics enabling a first user selection of one of the presentations of each said group, and a second user selection related to the presentation selected;

causing said computer to cause recordation of each of said first and second selections in a storage medium so as to generate a database of user choice information; and causing said computer to produce diet behavior analysis data based on the database of user choice information.

12. The method of claim 1 wherein said objects are selected from the group consisting of photographs and graphics.

13. The method of claim 1 wherein said presentations comprise written descriptive material.

14. The method of claim 1 wherein each of said groups comprises presentation of a plurality of objects.

15. The method of claim 1 wherein there are n pairs of objects.

16. The method of claim 15 wherein said pairs of objects comprise pairs of platters of food.

17. The method of claim 16 wherein said first user selection comprises selection of one of said platters.

18. The method of claim 17 wherein said second user selection comprises an indication of level of enthusiasm for the selected platter.

19. The method of claim 17 wherein the second user selection comprises an indication of frequency of consumption of a displayed food item.

20. The method of claim 19 further including the step of conducting diet training based on said behavior analysis.

21. The method of claim 20 wherein said step of conducting diet training includes the steps of displaying a meal and providing interactive user adjustment of portion size.

22. The method of claim 21 wherein said step of conducting diet training comprises the steps of user selection of displayed food items to create a meal, and display of nutritional characteristics of the displayed meal.

23. The method of claim 22 further including the step of user adjustment of portion size of the created meal.

24. The method of claim 1, wherein said one or more objects are food objects.

25. The method of claim 1 wherein said database is located at a website and said display is transmitted over the internet to a user.

26. The method of claim 1, wherein the diet behavior analysis data comprises relative preference for a plurality of groups.

27. The method of claim 1, wherein the diet behavior analysis data comprises relative enthusiasm for a plurality of food groups.

28. The method of claim 1, wherein the diet behavior analysis data comprises relative frequency of food preference for a plurality of food groups.

29. The method of claim 1, further comprising the step of displaying suggested dietary changes based on the diet behavior analysis data.

30. The method of claim 29, wherein the suggested dietary changes comprise a display of a suggested relative modification of consumption in a plurality of food groups.

31. The method of claim 1, where said diet behavior analysis further comprises comparing the specific information to a set of diet goals.

32. A system for conducting computerized visual diet training comprising:

a storage device comprising one or more food items based on a diet behavior analysis, where the diet behavior analysis comprises collecting and analyzing specific information on a user's instinctive eating tendencies and preferences;

a processor connected to the storage device, the processor being configured to perform the steps of:

accepting a user's selected food items from a choice of one or more food items, the selected food items corresponding to a meal;

accepting an estimate from the user of a value of a nutrient-related parameter of the selected food items; and displaying feedback to the user concerning the accuracy of the estimate.

33. The system of claim 32, wherein the food items are presented graphically.

34. The system of claim 33, wherein the processor is further configured to perform the step of adjusting a portion size of a food item based upon input by the user.

35. A system for conducting computerized visual diet training comprising:
  a storage device comprising one or more food items, where at least one food item is based on a diet behavior analysis, where the diet behavior analysis comprises collecting and analyzing specific information on a user's instinctive eating tendencies and preferences and comparing the specific information to a set of diet goals;
  a processor connected to the storage device, the processor being configured to perform the steps of:
    accepting a user's selected food items from a choice of the one or more food items, the selected food items corresponding to at least one meal;
    accepting an estimate from the user of a value of a nutrient-related parameter of the selected food items; and
    displaying feedback to the user concerning the accuracy of the estimate.

36. A system for diet behavior analysis, where the diet behavior analysis comprises collecting and analyzing specific information on a user's instinctive eating tendencies and preferences, comprising:
  a storage device including information enabling the display of one or more food items; and
  a processor connected to the storage device, the processor being configured to perform the steps of:
    displaying one or more groups of food items to a user;
    accepting a user's selected group from the one or more groups of food items;
    storing the selected group in a user choice database;
    repeating the displaying, accepting and storing steps; and
    performing the diet behavior analysis based on information stored in the user choice database.

37. The system of claim 36, wherein the groups of food items are stored in graphical form.

38. The system of claim 36, wherein two groups of food items are displayed to a user in the displaying step.

39. The system of claim 38, wherein each group consists of a single food item.

40. The system of claim 38, wherein each group comprises multiple food items.

41. The system of claim 36, wherein the processor is further configured to perform the steps of
  accepting an indication of a level of enthusiasm for the selected group; and
  storing the indicated level of enthusiasm in the user choice database.

42. The system of claim 36, wherein the processor is further configured to perform the steps of
  accepting an indication of a frequency of consumption for the selected group; and
  storing the indicated frequency of consumption in the user choice database.

43. The system of claim 36, wherein the processor is further configured to perform the step of conducting diet training based on the behavior analysis.

44. A system for diet behavior analysis, where the diet behavior analysis comprises collecting and analyzing specific information on a user's instinctive eating tendencies and preferences and comparing the specific information to a set of diet goals, comprising:
  a storage device including information enabling the display of one or more food items; and
  a processor connected to the storage device, the processor being configured to perform the steps of:
    displaying one or more groups of food items to a user;
    accepting a user's selected food items from a choice of the one or more groups of food items;
    storing the selected group of food items in a user choice database;
    repeating the displaying, accepting and storing steps; and
    performing the diet behavior analysis based on information stored in the user choice database.

* * * * *